(12) United States Patent
Brubacher (10) Patent No.: US 10,345,199 B2
(45) Date of Patent: Jul. 9, 2019

(54) SAMPLE ACQUISITION SYSTEM AND METHOD OF USE

(71) Applicant: SoBru Solutions, Inc., Fullerton, CA (US)

(72) Inventor: John Miles Brubacher, La Mirada, CA (US)

(73) Assignee: SoBru Solutions, Inc., Fullerton, CA (US)

( * ) Notice: Subject to any disclaimer, the term of this patent is extended or adjusted under 35 U.S.C. 154(b) by 585 days.

(21) Appl. No.: 14/775,236

(22) PCT Filed: Mar. 14, 2014

(86) PCT No.: PCT/US2014/029428
§ 371 (c)(1),
(2) Date: Sep. 11, 2015

(87) PCT Pub. No.: WO2014/153177
PCT Pub. Date: Sep. 25, 2014

(65) Prior Publication Data
US 2016/0047721 A1  Feb. 18, 2016

Related U.S. Application Data

(60) Provisional application No. 61/782,937, filed on Mar. 14, 2013.

(51) Int. Cl.
*C12Q 1/24* (2006.01)
*G01N 1/10* (2006.01)
(Continued)

(52) U.S. Cl.
CPC ............. *G01N 1/2035* (2013.01); *C12Q 1/24* (2013.01); *G01N 15/06* (2013.01); *G01N 1/2202* (2013.01);
(Continued)

(58) Field of Classification Search
CPC ...... B01D 21/265; C12Q 1/24; G01N 1/2035; G01N 15/60; G01N 1/2202; G01N 1/2247;
(Continued)

(56) References Cited

U.S. PATENT DOCUMENTS 3,555,910 A    1/1971  Spence et al.
4,383,917 A *  5/1983  Wells ........................ B04C 1/00
                                                                    209/723
(Continued)

OTHER PUBLICATIONS

International Search Report and Written Opinion PCT/US2014/029428, dated Aug 8, 2014.

*Primary Examiner* — William H. Beisner
*Assistant Examiner* — Danielle B Henkel
(74) *Attorney, Agent, or Firm* — Lodestone Legal Group; Jeromye V. Sartain (57) ABSTRACT

A system for acquiring a fluid sample from a flow pipe, comprising a sampling probe placed within the flow pipe, a curved separating pipe in fluid communication with the sampling probe, the separating pipe having formed therein an inwardly-opening lengthwise channel along the outside curve thereof, the separating pipe terminating in a sample area, and a lengthwise inwardly-opening sample passage in fluid communication between at least a portion of the sample area and a sample port, the sample passage being formed substantially opposite the channel, whereby inertial effects induced in the separating pipe cause relatively higher density inorganic and dead organic material to funnel into the channel and out a non-sample drain formed in the sample area substantially opposite the separating pipe while allowing live organisms to navigate the sample passage and out the sample port.

21 Claims, 6 Drawing Sheets

(51) Int. Cl.
*G01N 1/20* (2006.01)
*G01N 1/22* (2006.01)
*G01N 15/00* (2006.01)
*G01N 15/06* (2006.01)

(52) U.S. Cl.
CPC ... *G01N 1/2247* (2013.01); *G01N 2001/1012* (2013.01); *G01N 2015/0053* (2013.01); *G01N 2015/0065* (2013.01); *G01N 2015/0088* (2013.01)

(58) Field of Classification Search
CPC ... G01N 2201/1012; G01N 2015/0053; G01N 2015/0065; G01N 2015/0088
See application file for complete search history.

(56) References Cited

U.S. PATENT DOCUMENTS

| | | | |
|---|---|---|---|
| 5,811,696 A | 9/1998 | Jobson | |
| 7,111,521 B1 | 9/2006 | Andrews, Jr. | |
| 7,717,000 B2* | 5/2010 | Xie | B01F 5/0682 73/863.03 |
| 2008/0128331 A1* | 6/2008 | Lean | B03B 5/32 209/155 |
| 2009/0014360 A1* | 1/2009 | Toner | B01D 21/0087 209/208 |
| 2009/0114607 A1* | 5/2009 | Lean | B03B 5/626 210/779 |
| 2009/0170186 A1* | 7/2009 | Wu | B03C 5/026 435/286.1 |
| 2011/0271739 A1 | 11/2011 | Goohs et al. | |

* cited by examiner

SAMPLE ACQUISITION SYSTEM AND METHOD OF USE

RELATED APPLICATIONS

This application claims priority and is entitled to the filing date of U.S. Provisional application Ser. No. 61/782,937 filed Mar. 14, 2013, and entitled "Sample Acquisition System and Method of Use." The contents of the aforementioned application are incorporated herein by reference.

INCORPORATION BY REFERENCE

Applicant(s) hereby incorporate herein by reference any and all patents and published patent applications cited or referred to in this application.

TECHNICAL FIELD

Aspects of this invention relate generally to sampling systems, and more particularly to sample acquisition systems and methods of use relating to obtaining a fluid sample from a fluid flow.

BACKGROUND ART

By way of background, a number of industries are affected by regulations relating to water treatment, such as ballast water treatment systems ("BWTS") on ships and the like. Such regulations require that microorganisms be effectively rendered non-viable or non-living by the BWTS before such water is returned to the ocean or other body of water. Generally speaking, Zooplankton in the size range of approximately 10 to 50 microns or larger can be the "indicator" microorganism used to determine the effectiveness of treatment. Phytoplankton below 50 microns has also been employed as the indicator organism. To date, monitoring the effectiveness of such BWTS has largely been handled through samples submitted to a lab, there most often involving human examination under a microscope, and the samples themselves being obtained "off-line" as in a collection tank and then having a delay from the sample acquisition event to any manipulation or evaluation of the sample. As such, these laboratory approaches to sample acquisition and compliance assessment have numerous shortcomings in terms of accuracy, speed, and cost. Similarly, flow cytometry systems can offer relatively higher throughput, but not necessarily for real time direct enumeration of live vs dead zooplankton levels, due to a significant amount of man-in-the-loop sample preparation. Fundamentally, neither such prior art approaches provide a mechanism for sorting living organisms from non-living or inorganic matter within the sample as part of the acquisition system or otherwise in an automated form in "real time" or through "on-line" sampling from a fluid flow. The present invention improves and renders deployable the sample acquisition process in meeting these needs and provides further advantages over prior art sampling systems and approaches. The subject invention, though again in the context of BWTS compliance testing, may be practiced in a wide array of contexts and so is not limited to the exemplary BWTS context (for example, ocean, lake, river and stream testing as well as air or other fluid testing). Thus, while "water" is discussed throughout as the sampled fluid, it is to be understood that the invention is not so limited and other fluids may be sampled as well, again depending on the context.

DISCLOSURE OF INVENTION

Aspects of the present invention teach certain benefits in construction and use which give rise to the exemplary advantages described below.

The present invention solves the problems described above by providing a new and novel system and method for acquiring a fluid sample from a flow pipe. The system provides, in the exemplary embodiment, a sampling probe placed within the flow pipe, a curved separating pipe in fluid communication with the sampling probe, the separating pipe having formed therein an inwardly-opening lengthwise channel along the outside curve thereof, the separating pipe terminating in a sample area, and a lengthwise inwardly-opening sample passage in fluid communication between at least a portion of the sample area and a sample port, the sample passage being formed substantially opposite the channel, whereby inertial effects induced in the separating pipe cause relatively higher density inorganic and dead organic material to funnel into the channel and out a non-sample drain formed in the sample area substantially opposite the separating pipe while allowing live organisms to navigate the sample passage and out the sample port.

A primary objective inherent in the above described system and method of use is to provide advantages not taught by the prior art.

Another objective is to provide such a system and method wherein the separating pipe is substantially helically curved, in at least one embodiment.

Another objective is to provide such a system and method wherein the sample passage is formed having a blocking chute suspended therein, in at least one embodiment.

Another objective is to provide such a system and method wherein an attractant is positioned within the sample area substantially adjacent the sample passage or the sample port, in at least one embodiment.

Another objective is to provide such a system and method wherein a repellant is positioned within the sample area substantially adjacent the non-sample drain, in at least one embodiment.

Another objective is to provide such a system and method wherein the sampling probe is an isokinetic probe, in at least one embodiment.

Another objective is to provide such a system and method wherein a bubble collapsing screen is positioned within the flow pipe upstream of the distal sampling tip orifice.

Other features and advantages of aspects of the present invention will become apparent from the following more detailed description, taken in conjunction with the accompanying drawings, which illustrate, by way of example, the principles of aspects of the invention.

BRIEF DESCRIPTION OF DRAWINGS

The accompanying drawings illustrate aspects of the present invention. In such drawings.

The above described drawing figures illustrate aspects of the invention in at least one of its exemplary embodiments, which are further defined in detail in the following description. Features, elements, and aspects of the invention that are referenced by the same numerals in different figures represent the same, equivalent, or similar features, elements, or aspects, in accordance with one or more embodiments.

MODES FOR CARRYING OUT THE INVENTION

The above described drawing figures illustrate aspects of the invention in at least one of its exemplary embodiments, which are further defined in detail in the following description.

Figure 1:
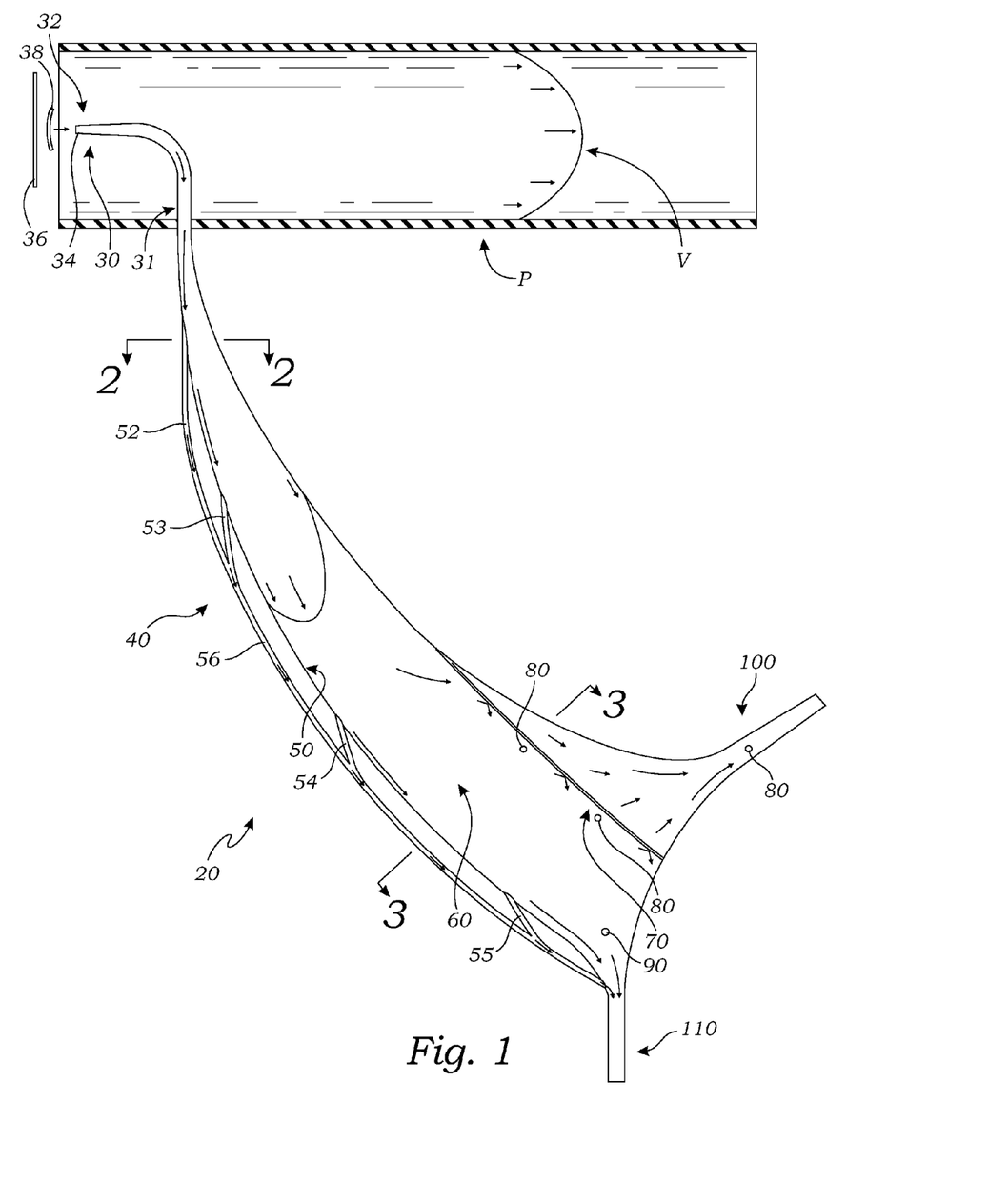
FIG. 1 is a schematic view of an exemplary sample acquisition system, in accordance with at least one embodiment.
Figures 2, 3, 4:
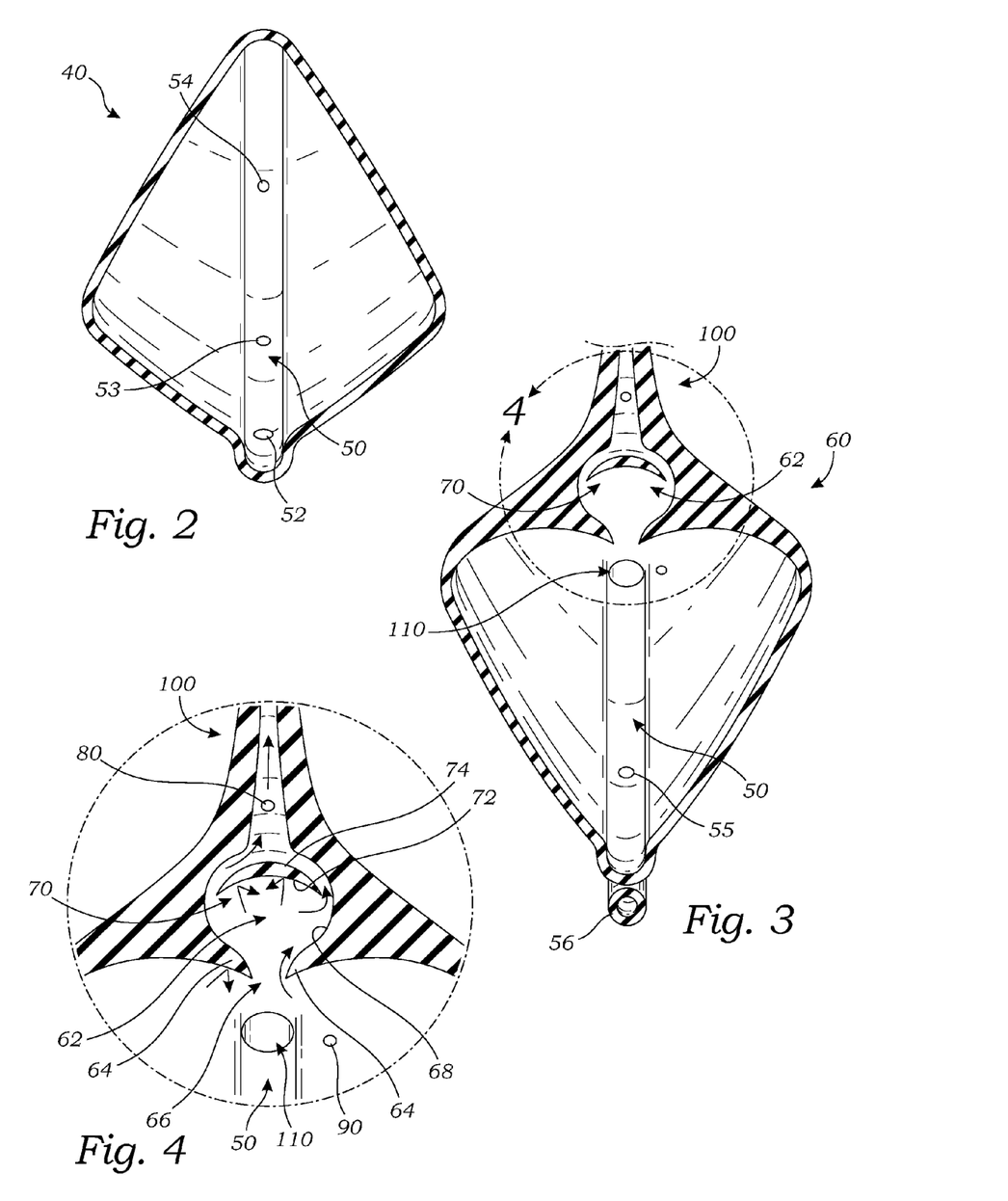
FIG. 2 is an enlarged schematic sectional view thereof taken along line "2-2" of FIG. 1, in accordance with at least one embodiment.
FIG. 3 is an enlarged schematic sectional view thereof taken along line "3-3" of FIG. 1, in accordance with at least one embodiment.
FIG. 4 is an enlarged partial schematic sectional view thereof taken from circle "4" of FIG. 3, in accordance with at least one embodiment.
Figure 5:
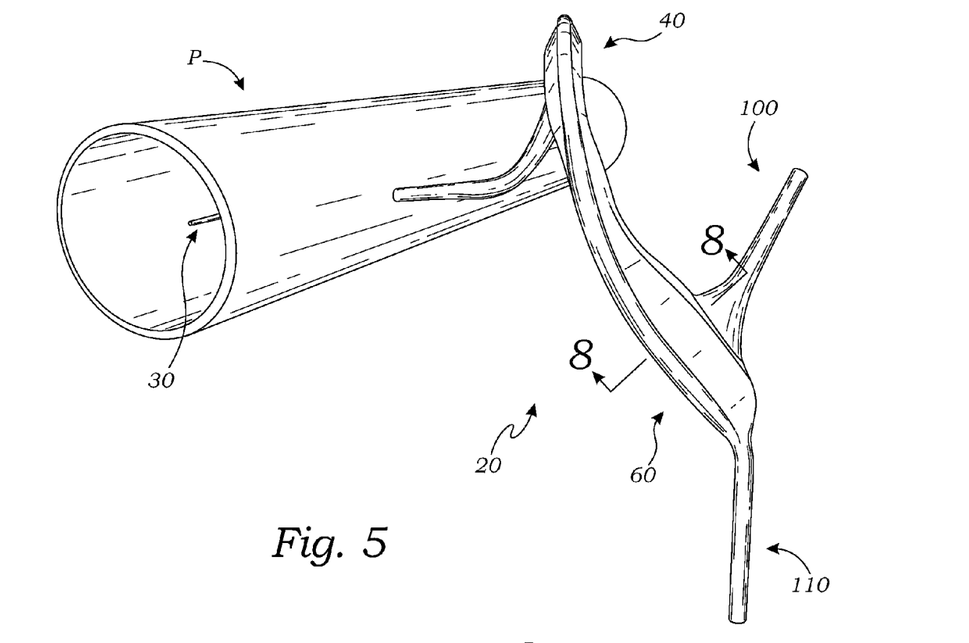
FIG. 5 is a perspective view of an alternative exemplary sample acquisition system, in accordance with at least one embodiment.
Figure 6:
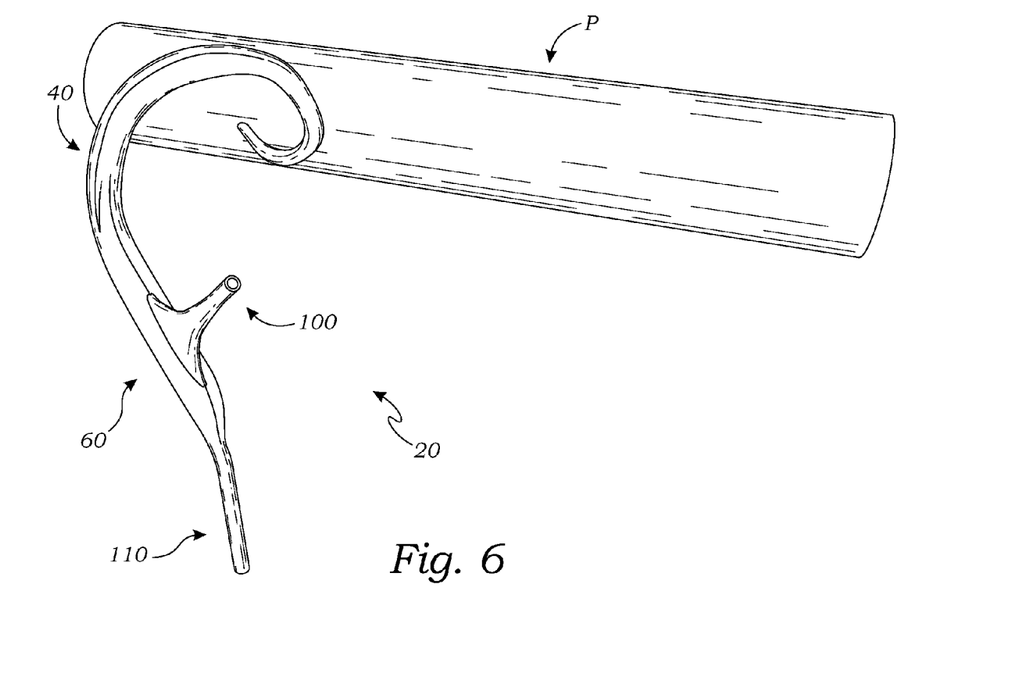
FIG. 6 is a further perspective view thereof, in accordance with at least one embodiment.

As an overview, and with reference to the schematic view of FIG. 1, the exemplary sample acquisition system 20 has eight main hardware components or sections, which are discussed in turn below: a sampling probe 30 installed in a flow pipe P; a separating pipe 40 having a first cross-section as shown in FIG. 2; a channel 50 of the separating pipe 40 in which are incorporated particle returns 52, 53, 54 and 55; a sample area 60 of the separating pipe 40 having a second cross-section as shown in FIG. 3; a sample blocking chute 70; attractants 80 and/or repellants 90; a sample port 100; and a non-sample drain 110. There are related tanks, tubes, filters, pumps, and other aspects, whether or not shown, that may facilitate the collection and processing of the water sample, which could be necessary in particular contexts but are nevertheless ancillary components that can be substituted for by other equivalent structure now known or later developed and so are not the focus of the present invention. It will be appreciated by those skilled in the art that the exact configuration of the system and its eight main sections or features may take a number of forms to suit particular applications without departing from the spirit and scope of the present invention. Accordingly, it will be further appreciated that the configurations of the system shown and described are exemplary and that the invention is not so limited. Features, elements, and aspects of the invention that are referenced by the same or similar names or numerals or depicted in similar fashion in different views represent the same, equivalent, or similar features, elements, or aspects, in accordance with one or more embodiments.

Turning now to FIG. 1, there is shown a schematic side view, not to scale, of an exemplary embodiment of a sample acquisition system 20 according to aspects of the present invention. Going in sequence as a water sample would be obtained and processed through the system 20, and thus starting upstream of the sampling probe 30, an illustrative flow pipe P cross-section having a flow therethrough from left to right in the schematic is shown as having a pipe fluid velocity profile V therein (though shown downstream of the sampling probe 30 for ease of illustration, it will be appreciated that such velocity profile would be substantially consistent along such a pipe of roughly consistent dimension and inner surface), which velocity profile V those skilled in the art will appreciate is dictated by a number of factors such as the pipe diameter and inner surface characteristics and the kind of fluid passing therethrough. The sampling probe 30 is identified in the exemplary embodiment as "isokinetic," which is generally a term of art relating to sampling of a fluid stream at substantially the same rate at which the stream is approaching the sample nozzle (i.e., that the velocity or flow rate of the sample acquisition flow is substantially the same as that of the flow being sampled), which is beneficial in providing a representative sample particularly where particulates are carried in the fluid stream. It will be appreciated by those skilled in the art that the sampling probe 30 may or may not be "isokinetic" in the strictest sense, such that the present invention is not so limited, though the principle of isokinetic sampling has nevertheless been taken into account in the selection or configuration of the sampling probe 30 and the overall sample acquisition system 20. As shown, the sampling probe 30 is effectively positioned within the flow pipe P such that a distal end 32 thereof defining the intake tip or inlet or sampling orifice 34 of the probe 30 is substantially parallel to the fluid flow or the walls of the flow pipe P and is further positioned substantially centered therein, or substantially along the centerline or axis of the flow pipe P where it will be appreciated is typically the location of maximum fluid velocity. In order to support lower frictional losses, the inside cross-sectional area of the sampling probe 30 will be increased or tapered so that the fluid velocity of the sample will be decreased for the majority of the length of the probe 30, which increase in cross-section will occur gradually enough in order to not generate too much turbulence within the probe. In the exemplary embodiment the sampling orifice 34 has an inside diameter of approximately 4 mm tapering gradually to a sampling probe inside diameter of approximately 20 mm, though it will be appreciated that virtually infinite variations on such dimensions are possible. The tip of the probe 30 will preferably maintain the required velocity for only a short distance, such that in the exemplary embodiment its length is only approximately three (3) inside diameters. A control system (not shown) will maintain the proper sampling flow relative to the fluid velocity in close proximity to the sampling probe 30, preferably substantially the same, slightly greater or slightly less than the local fluid velocity. As such, a local velocity sensor (not shown) may be operably installed integral to or substantially adjacent to the sampling probe 30, such as near the tail end of the sampling probe 30, which velocity sensor will preferably have a design or profile that will eliminate or reduce any significant turbulence that could impact the integrity of the velocity data from the sensor or the representative sampling characteristics of the isokinetic probe. In order to maintain adequate probe performance with minimal maintenance, forward mounted devices may be installed within the flow pipe P to protect the sampling probe 30 from possible conditions found in the pipework. For example, a debris screen 36 may be installed in the flow pipe P upstream of the sampling probe inlet 34 so as to deflect or trap larger objects and so deter them from hitting the probe 30. Such a debris screen 36 may be on the order of 10 mm mesh. A bubble collapsing screen 38 may also be provided, illustrated as positioned between the debris screen 36 and the sampling probe inlet 34, for the purpose of mitigating the effects bubbles might have on sample integrity and so having on the order of a 2 mm mesh size, for example. Such screens 36, 38 may be suspended within the pipe P using any mounting means now known or later developed, though preferably having a relatively small and streamlined profile so as to minimize any disturbance to or creation of turbulence in the fluid flow. In the exemplary embodiment, the sampling probe 30 beyond the inlet or intake section then bends substantially ninety degrees (90°) so as to extend perpendicular to the flow and pass through the wall of the flow pipe P as shown. Those skilled in the art will appreciate that all such exemplary configurations and dimensions are merely illustrative of aspects of the present invention and non-limiting. Rather, any such flow pipe and sampling probe configurations now known or later developed may be practiced in conjunction with the present invention without departing from its spirit and scope.

Turning next to the separating pipe 40, it is shown as being in fluid communication with the proximal end 31 of the sampling probe 30 and as being generally configured having a gradually expanding and curving profile, more about which will be said and appreciated from the below discussion. In principle, the separating pipe 40 is to be configured to decelerate or slow the sample and so allow any relatively higher density inorganic and dead organic material suspended in the fluid sample to be separated from that portion of the fluid sample containing any relatively lower density live microorganisms. The primary velocity vector in the separating pipe 40 is towards the outside of the curve, which causes the relatively higher density material to travel along the outside curve of the separating pipe 40, or that portion of the pipe generally to the left as shown in the schematic, which thus defines an outside channel 50 along the separating pipe 40. In contrast, due to a greater drag-to-mass ratio, among other things, the relatively lower density live and more buoyant microorganisms would tend to move towards the relatively lower velocity inside of the curve, or that portion of the separating pipe 40 generally to the right as shown in FIG. 1. To enhance this process, in the exemplary embodiment, the inside of the curve may be formed of or coated or otherwise treated so as to have a relatively higher friction surface and the outside of the curve to have a relatively lower friction surface. The result in one aspect of the invention, then, is a curve of the separating pipe 40 defining a velocity profile that has a relatively greater velocity closer to the outside of the curve. With reference to the separating curve cross-section shown in FIG. 2, which would be representative of the upper section of the separating pipe 40 between the sampling probe 30 and the sample area 60, more about which is said below, it is to be appreciated that the separating pipe 40 upper portion is in the exemplary embodiment effectively tapered from the sampling probe 30 to the sample area 60, such that the cross-section of FIG. 2 is to be understood as merely illustrative, it being further noted once more that the schematic is not to scale. In the exemplary embodiment of the separating curve upper cross-section, integral to the shape of the separating pipe 40 is a particle channel 50 on the outside of the curve as shown, which channel helps direct the higher velocity flow that may contain inorganic and dead organic matter toward the non-sample drain 110. The cross-section has a substantially "triangular" or "wedge" shape on the inside of the curve that provides an overall larger surface area and thus greater frictional area to facilitate lower fluid velocity, which surfaces may again be relatively higher-friction as well. Opposite the "triangular" profile inside curve of the separating pipe 40 there is shown a "dome" shape towards the outside of the curve that facilitates "focusing" the relatively higher density particles to the outside of the curve that may then be "captured" by the particle channel 50, which "domed" surface and the particle channel 50 itself may again be relatively low-friction. In this way, the flow containing a relatively higher concentration of relatively higher density inorganic and dead organic material is accelerated to the outside of the separating pipe 40, and the separating curve cross-section, specifically, so as to pull or sweep such fluid and material downwardly toward the non-sample drain 110.

With continued reference to FIG. 1 and now with reference to the enlarged section view of FIG. 3, the flow so divided or beginning to separate then passes out of or transitions from the separating pipe 40 into the sample area generally denoted 60 shown in the schematic as substantially at the bottom of the system 20, or downstream of the separating pipe 40. Integral to the sample area 60 is the continued separation between the relatively higher and lower density material wherein the overall velocity in this section is relatively low, such that any frictional losses are not significant, and the particle channel 50 formed at the outer curve continues to separate the higher density non-living particles, while the live organisms are drawn into or swim toward the "safety" of the inner sample passage 62, more about which is said below. As shown in FIG. 3, the sample area 60 has an exemplary cross-section wherein the particle channel 50 is still formed substantially at the outside curve of the profile, only now that outside curve having transitioned in the exemplary embodiment from a "dome" shape as in the separating pipe 40 into more of an inverted triangle opening toward the substantially opposite sample passage 62, so as to effectively funnel the relatively higher density dead or inorganic matter in the sample flow down into the channel 50 and away from the sample passage 62 and ultimately out through the non-sample drain 110. More particularly, in a further exemplary aspect of the invention, the particle channel 50 is formed having one or more particle returns 52, 53, 54, and 55, each of which functionally provides an effective trap and feeds a particle return line 56 as a means for the particles to bypass all or part of the sample area 60 altogether. It will be appreciated that any such structure and associated function of the particle channel 50 spanning one or both of the separating pipe 40 and the sample area 60 for the purpose of separating and readily flowing the sample containing proportionately higher dead or inorganic particles may be employed in the present invention without departing from its spirit and scope. In the exemplary embodiment, the schematic again not being to scale, the distance across the sample area 60 is approximately fifty to two hundred millimeters (50-200 mm), though this will be appreciated as merely illustrative.

Referring still to FIGS. 1 and 3, attention is next drawn to the sample intake passage 62 and associated blocking chute 70, which together facilitate separation out of the flow of the relatively lower density live organisms "swimming" around the chutes as they resist downward movement while the relatively higher density dead organisms and inorganic material is channeled down to the bottom and out. Particularly, it is expected that the more buoyant organic material will move through the sample passage 62 and around the blocking chute 70 as the buoyancy force vector resists going down the chutes. A significant characteristic of the sample area 60 that facilitates these functions is low velocity of the fluid, particularly in and around the sample passage 62 and the sample blocking chute 70. This will minimize any forces generated as the fluid moves around the chute 70, requiring self-induced or buoyant forces for successful negotiation around the obstructions. In the exemplary embodiment, the sample blocking chute 70 is effectively shaped so as to be narrow enough to allow live microorganisms to easily bypass the chute 70, wide enough to effectively guide the higher density material down to the bottom of the sample are 60, and long enough to both capture and guide higher density material to the non-sample drain 110 at the bottom. Such a "drop chute" system will not necessarily be one hundred percent effective, but the "chutes"—both the sample blocking chute 70 and the outer channel 50—are nevertheless effective in minimizing the transportation of inorganic or dead organic material into the sample analysis system (not shown). With reference again to the cross-sectional view of FIG. 3 and now the further enlarged cross-sectional view of FIG. 4 representative of the sample blocking chute 70, by way of further explanation regarding the exemplary embodiment, the sample passage 62 may be configured to effectively form a "non-linear path," or a flow path around the central blocking chute 70 only readily navigated by living organisms, as by leaving a gap or space between the edges of the blocking chute 70 and the interior sample passage surface 68. This is further accomplished in the illustrated embodiment by forming an opening or inlet 66 in the sample passage 62 as defined by opposing sample passage lips 64 that is narrower than the blocking chute 70 is wide, such that, as shown, dead or non-organic particles, which generally only move in a straight line and are non-motive, may be deflected off of the surfaces or lips 64 around the inlet 66 or off of the concave inwardly-facing surface 72 of the blocking chute 70 and back into the sample area 60, or effectively down the sample area 60 along the blocking chute 70 toward the non-sample drain 110, while once again live organisms, which are to some extent motive, or exhibit self-induced motion, and are subject to buoyancy forces and can thus move in non-straight lines, would tend to move around an obstacle such as the blocking chute 70 and thus pass through the sample passage 62 and on to the sample port 100 as shown. In the exemplary embodiment, the blocking chute has a substantially convex or sloped outwardly-facing surface 74 opposite the inwardly-facing surface 72 and the sample port 100 tapers down or has a progressively reduced inside diameter or dimension so as to speed the flow back up therethrough.

The sample port 100 is effectively the inlet to the microorganism analysis section (not shown), which may be any appropriate such testing or analysis device or system now known or later developed, including but not limited to the "Microorganism Evaluation System" disclosed in a co-pending international PCT patent application filed by the same inventor on Jun. 18, 2013, and assigned Int'l. App. No. PCT/US2013/046334, which itself claims priority to a U.S. provisional patent application filed on Jun. 18, 2012, and assigned Ser. No. 61/661,011. Additional details regarding such an analysis system are further disclosed in co-pending U.S. provisional patent applications by the same inventor entitled "Microorganism Evaluation System Viewing Section" filed on Dec. 16, 2013, and assigned Ser. No. 61/916,343, and entitled "Microorganism Sorting System and Method" filed on Jan. 24, 2014, and assigned Ser. No. 61/931,412. Within or in front of the sample port 100 substantially upstream of any such microorganism analysis section, a wire mesh (not shown) may be located in order to prevent larger material from obstructing the analysis section. Again, the only other passage out of the system 20 is effectively the non-sample drain 110 at the bottom, where the water or other fluid containing substantially higher amounts of dead or inorganic material passes from the system 20. The pump (not shown) that supports this section will be able to pass the particulate material that collects down in this portion of the system 20, or that passes through the non-sample drain 110. Furthermore, the control system will vary the flow rate out through the drain 110 in order to indirectly, though effectively, meet the sample flow requirements going out through the sample port 100, as it will be appreciated that the flow rate through one will affect the flow rate through the other within this effectively closed system. In one embodiment, for at least this purpose of regulating flows, a fluid velocity sensor (not shown) may be located in the tube (not shown) downstream of the sample port 100 in order to measure the sample flow rate and provide such feedback to the control system. In the exemplary embodiment, with the flows out of the sample port 100 and the non-sample drain 110 so regulated, and with an overall system 20 substantially configured as shown, it is expected that approximately fifty to ninety percent (50-90%) of the total fluid volume or flow will exit the sample port 100 and approximately ten to fifty percent (10-50%) of the total fluid volume or flow will exit the non-sample drain 110. Those skilled in the art will appreciate that all such flow distributions are merely illustrative of aspects of the present invention and are expressly non-limiting.

With continued reference to FIGS. 1-4 illustrating an exemplary embodiment of the present invention, attractants 80 may be positioned within the sample area 60 substantially along the sample passage 62 for the purpose of drawing or attracting live organisms to the sample port area. Such attractants 80 may be a remote light source emitting a spectrum of light energy that live organisms are drawn to, shining through the sample passage 62 around the blocking chute 70 and through the sample passage inlet 66 and/or along the inlet 66, such as spaced along the sample passage lips 64, thereby somewhat simulating sunlight, or moonlight, or green "phytoplankton" through crevasses of a rock. For example, a wavelength of approximately 530 nm (green) appears to be effective as an attractant relative to representative organisms such as zooplankton. Simulated "plant life" could also be attractive, and also add fluid damping and act as additional flow control guides into the sample port area. Similarly, repellants 90 may be positioned within the sample area 60 substantially adjacent or at least in the vicinity of the non-sample drain 110 for the purpose of repelling living organisms from the non-sample drain 110. For example, the repellant(s) 90 could comprise a particular acoustic source that would simulate a predator, with the idea being to cause the microorganisms to "fear" and "flee" the non-sample drain area. Once more, those skilled in the art will appreciate that other such attractants and repellants may be employed in a variety of ways and locations within the sample acquisition system 20 without departing from its spirit and scope.

More generally, the disclosed sample acquisition system 20 or other equivalent structure facilitates improved performance through: (i) substantially real-time and on-line sample acquisition based on an isokinetic-type fluid flow sampling; (ii) efficient and effective separation of live organisms from dead or inorganic material within the sample; and (iii) removal of a significant amount of non-live material prior to sample evaluation. Further, such a sample acquisition system exhibits relatively minimal inertial excitation of the sample, minimal latency, and system bypass when crossing low turbidity waters, such as an open ocean with no river influence.

Figures 7, 8, 9:
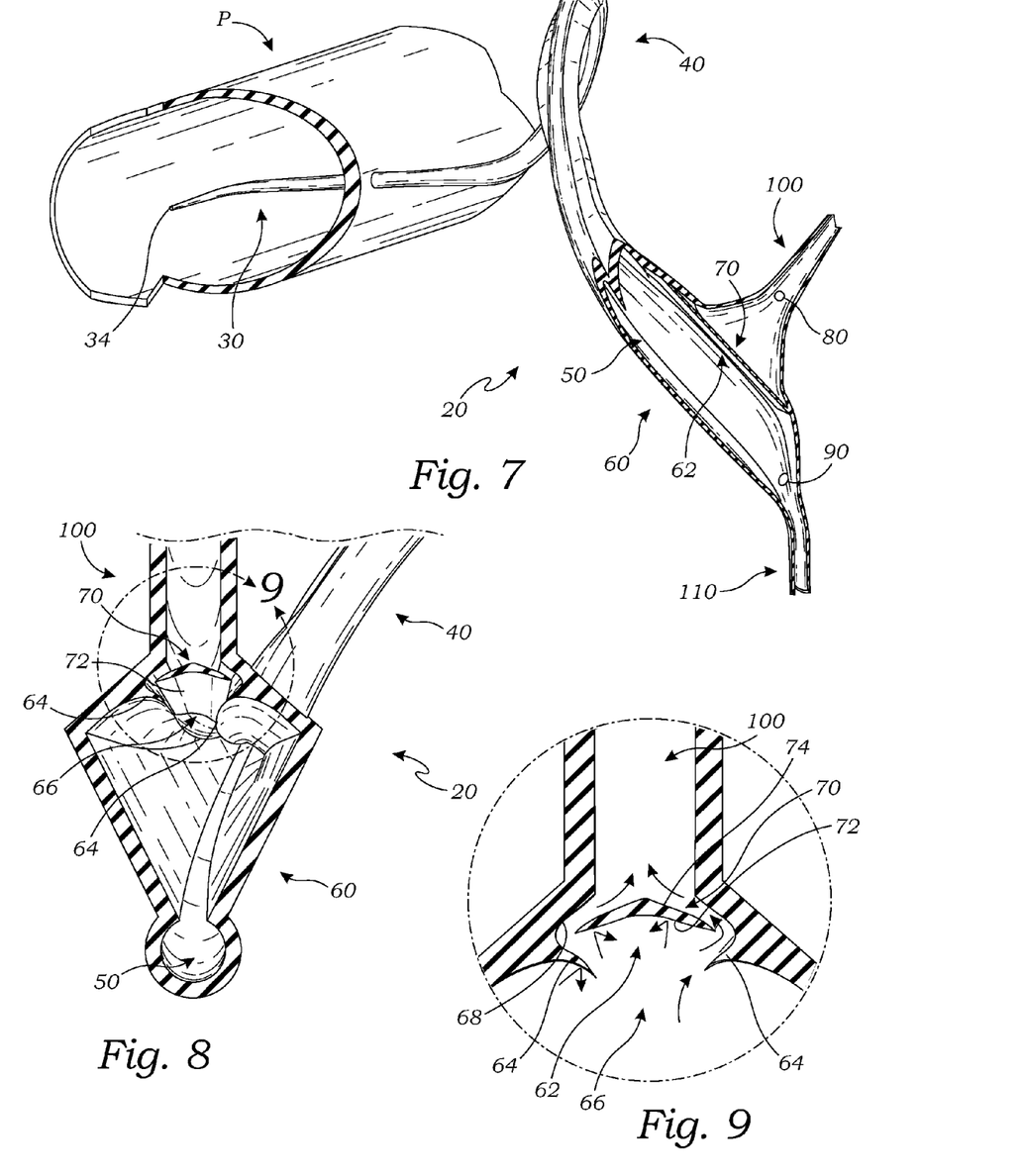
FIG. 7 is a further, partially cut-away perspective view thereof, in accordance with at least one embodiment.
FIG. 8 is an enlarged, partial, sectioned perspective view thereof taken along line "8-8" of FIG. 5, in accordance with at least one embodiment.
FIG. 9 is a further enlarged, partial, sectioned schematic view thereof taken from circle "9" of FIG. 8, in accordance with at least one embodiment.

Turning now to FIGS. 5-9, there are shown various perspective or sectioned views of an alternative sample acquisition system 20 according to aspects of the present invention. Once more, the system 20 generally comprises a sampling probe 30 in fluid communication with a separating pipe 40 that itself is in fluid communication with and transitions to a sample area 60 wherein the separation of live organisms from dead organisms or inorganic matter is facilitated as above-described. As will be appreciated particularly from the perspective views of FIGS. 5 and 6, in the alternative exemplary embodiment, once exiting the flow pipe P, the separating pipe 40 twists through approximately a three hundred-fifteen degree (315°) helix, the twisting pipe causing inertial effects as the fluid flows therethrough, whereby the fluid flow is accelerated or has a relatively higher velocity along the outside of the curve, thus encouraging the relatively higher density dead or inorganic matter toward the outside of the curve, while the flow is relatively slower toward the inside of the curve. Again, geometric and material selections and/or optional surface treatments may further enhance the frictional and thus velocity effects to assist in encouraging the described separation. It will be appreciated by those skilled in the art that while a particular shape and helix of the separating pipe 40 is shown and described the invention is not so limited; rather, a variety of other geometries of the separating pipe 40 are possible without departing from its spirit and scope. As previously indicated, though not shown, the sample port 100 would lead to a downstream microorganism analysis section (not shown) and the non-sample drain 110 would simply discharge to a tank (not shown) or otherwise be taken out of the system 20 or any related analysis section (not shown). The optional debris screen 36 and bubble collapsing screen 38 shown in FIG. 1 as being adjacent the sampling tip 34 are not shown in FIGS. 5 and 7 for simplicity. An attractant 80 such as a light source may again be positioned within the sample port 100 downstream of or behind the sample passage 62 and blocking chute 70 and a repellant 90 such as an acoustic device may be positioned near the bottom of the sample area 60 in the vicinity of the non-sample drain 110, as shown in FIG. 7. As best seen in the enlarged partial cross-sectional view of FIG. 8, the sample area 60 is again formed having a profile that substantially approximates an inverted triangle, thereby effectively speeding and funneling the outer flow toward, into, and through the discharge channel 50 and slowing the inner flow due to geometric and frictional effects and thereby allowing relatively lower density living organisms to make their way into the sample passage 62 and around the blocking chute 70 and into the sample port 100 for downstream processing. Particularly regarding the sample passage 62, and with further reference to the further enlarged partial sectional schematic view of FIG. 9, which it will be appreciated is effectively a "slice" of the component as sectioned in FIG. 8 with the remaining features behind the "slice" removed for simplicity so as to more clearly see the features of the sample passage 62, there is again shown a relatively narrower sample passage inlet 66 formed between opposite sample passage lips 64 and a concave downwardly- or inwardly-facing surface 72 of the blocking chute 80 cooperating to deflect and direct toward the lower non-sample drain 110 (FIG. 7) any dead or inorganic matter, with basically only living organisms navigating the sample passage 62 around the margins of the blocking chute 70 between it and the inside surface 68 of the passage 62 and then out through the sample port 100 as shown. It will once again be appreciated by those skilled in the art that while a particular configuration of the sample passage 62 and blocking chute 70 effectively suspended therein are shown and described, the invention is not so limited, but may take a number of other forms without departing from its spirit and scope.

Figure 10:
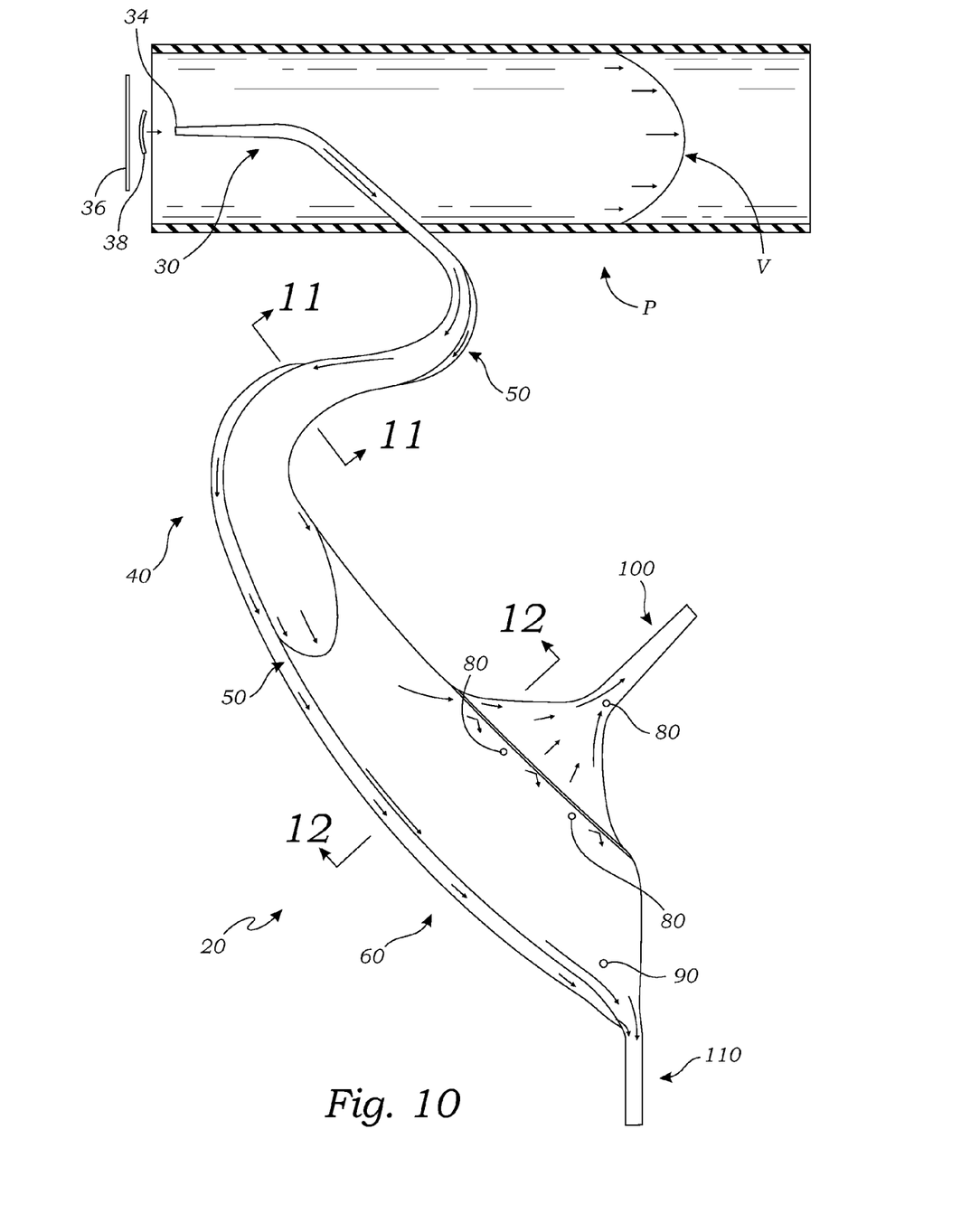
FIG. 10 is a schematic view of the alternative exemplary sample acquisition system of FIG. 5, in accordance with at least one embodiment.
Figures 11, 12, 13:
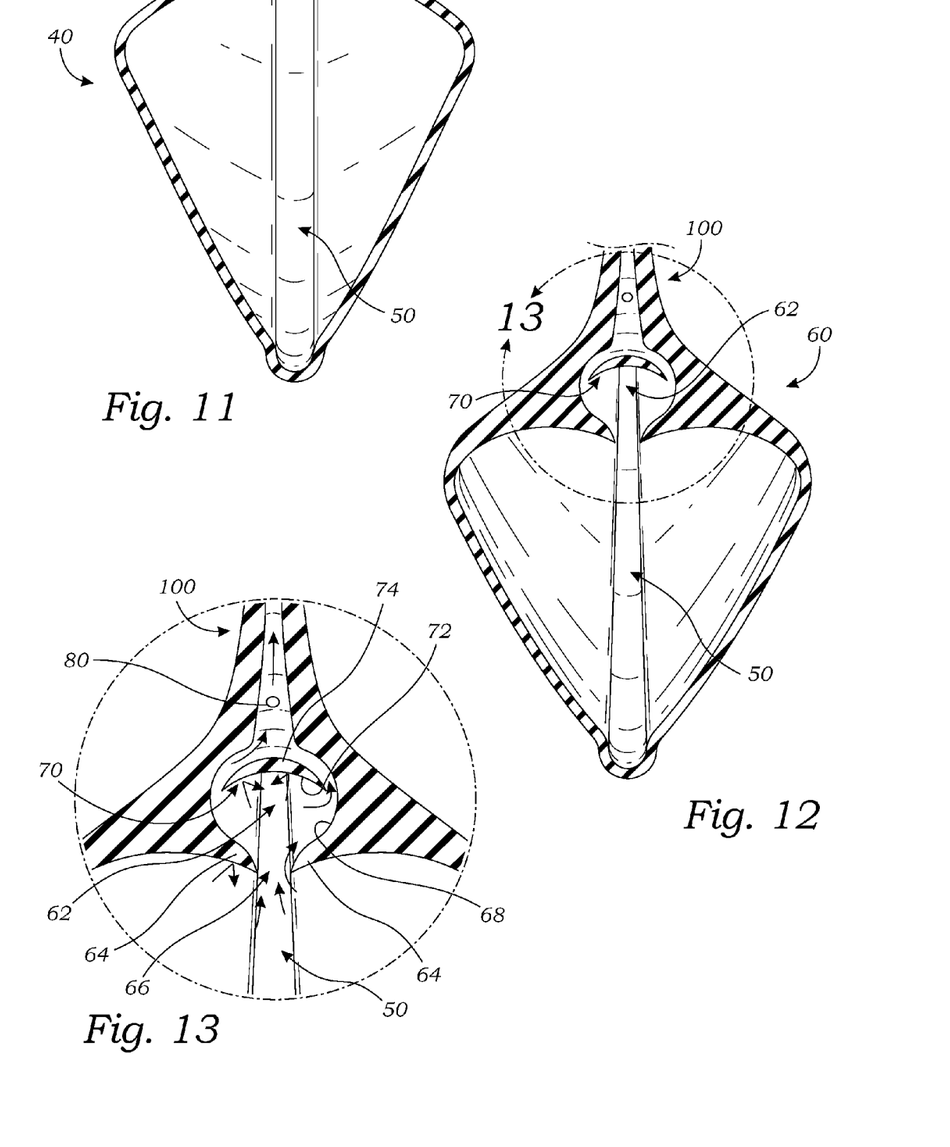
FIG. 11 is an enlarged schematic sectional view thereof taken along line "11-11" of FIG. 10, in accordance with at least one embodiment.
FIG. 12 is an enlarged schematic sectional view thereof taken along line "12-12" of FIG. 10, in accordance with at least one embodiment.
FIG. 13 is an enlarged partial schematic sectional view thereof taken from circle "13" of FIG. 12, in accordance with at least one embodiment.

Finally, referring now to the schematics of FIGS. 10-13, which are somewhat analogous to those of FIGS. 1-4, though here effectively corresponding to the alternative exemplary embodiment of FIGS. 5-9, it can first be seen that the sampling probe 30 beyond the inlet or intake section tip 34 then bends substantially forty-five degrees (45°) so as to extend rearwardly in the flow and pass through the wall of the flow pipe P still at a substantially forty-five-degree angle as shown. It will be appreciated that such an angle of the sampling probe 30 may facilitate transition to the helical separating pipe 40 and introduce relatively less turbulence to the passing main fluid flow, or certainly would shift any such turbulence or disturbance to the representative or normalized velocity profile V further downstream of the probe inlet 34 and any related flow sensor (not shown). Those skilled in the art will once again appreciate that other geometrical configurations of the probe 30 are possible without departing from the spirit and scope of the invention. Next, regarding the separating pipe 40, the channel 50 is again shown as following the twist so as to remain substantially at the outer part of the curve and thereby capture and direct downwardly through the system 20 the relatively higher density dead and inorganic material that preferably does not make its way into the analysis section by way of the sample passage 62 of the sample area 60 and the downstream sample port 100. Once more, attractants 80 may be positioned in one or more locations adjacent or behind the sample blocking chute 70 to further encourage living organisms into and through the sample passage 62, whereas repellants 90 may be positioned near the lower end of the sample area 60 to discourage living organisms from approaching the non-sample drain 110. As can be seen in FIG. 10 particularly, in the alternative embodiment, there are no traps or particle returns and lines 52-56 as in the embodiment of FIGS. 1-4, here the discharge flow simply passing at relatively higher velocity down through the channel 50 in the outer curve. Furthermore, as shown in the section view of FIG. 11 taken through a representative profile of the separating pipe 40, distinct from the somewhat analogous section view of FIG. 2, the pipe 40 is here shown as having the inverted triangle or "V" opening toward the substantially opposite sample passage 62 and so pointing or having its apex toward the channel 50, so as to effectively funnel the relatively higher density dead or inorganic matter in the sample flow down into the channel 50 and away from the sample passage 62 as previously described. In this way, and with further reference to the sectional view of FIG. 12, in the alternative embodiment, the pipe 40 and sample area 60 maintain a more constant, even if tapering, profile along the length of the device maintaining the relatively narrower "V" portion of the profile directed at or funneling toward the channel 50 at the "outside" of the curve where the flows are relatively faster, with the more "dome-shaped" portion of the profile remaining toward the "inside" of the curve where the flows are relatively slower, such "dome-shaped" inside wall eventually transitioning and giving way to the opening 66 to the sample passage 62 through which the living organisms move about the suspended blocking chute 70. It will be appreciated by those skilled in the art that a variety of configurations and arrangements of the components of the sample acquisition system 20 according to aspects of the present invention are possible without departing from its spirit and scope, such that the disclosed embodiments and particular shapes of the separating pipe 40 and sample area 60 are to be understood as merely illustrative.

To summarize, regarding the exemplary embodiments of the present invention as shown and described herein, it will be appreciated that a sample acquisition system is disclosed as configured for substantially real-time sampling from a fluid flow with an effective means for readily then separating dead or inorganic material from the sample before evaluation. Because the principles of the invention may be practiced in a number of configurations beyond those shown and described, it is to be understood that the invention is not in any way limited by the exemplary embodiments and is able to take numerous forms without departing from the spirit and scope of the invention. Furthermore, the various features of each of the above-described embodiments and components may be combined in any logical manner and are intended to be included within the scope of the present invention. It will also be appreciated by those skilled in the art that the present invention is not limited to the particular geometries and materials of construction disclosed, but may instead entail other functionally comparable structure, now known or later developed, without departing from the spirit and scope of the invention.

While aspects of the invention have been described with reference to at least one exemplary embodiment, it is to be clearly understood by those skilled in the art that the invention is not limited thereto. Rather, the scope of the invention is to be interpreted only in conjunction with the appended claims and it is made clear, here, that the inventor believes that the claimed subject matter is the invention.

What is claimed is:

1. A system for acquiring a fluid sample from a flow pipe, comprising:
    a sampling probe placed within the flow pipe;
    a separating pipe in fluid communication with the sampling probe, the separating pipe being substantially helically curved and having formed therein an inwardly-opening lengthwise channel along the outside curve thereof, the separating pipe terminating in a sample area; and
    a lengthwise inwardly-opening sample passage in fluid communication between at least a portion of the sample area and a sample port, the sample passage being formed substantially opposite the channel and being further formed with a substantially lengthwise blocking chute suspended therein, the blocking chute being substantially parallel to the channel across the sample area, whereby inertial effects induced in the separating pipe cause relatively higher density inorganic and dead organic material to funnel into the channel and out a non-sample drain formed in the sample area substantially opposite the separating pipe while allowing live organisms to navigate the sample passage around the blocking chute and out the sample port.

2. The system of claim 1 wherein the blocking chute is formed having a substantially concave inwardly-facing surface, whereby inorganic and dead organic material is deflected off the inwardly-facing surface and otherwise funneled therealong toward the non-sample drain in cooperation with the channel.

3. The system of claim 2 wherein:
    the sample passage is formed having an interior sample passage surface; and
    the blocking chute is substantially spaced from the sample passage surface so as to form fluid flow pathways about the blocking chute through the sample passage.

4. The system of claim 2 wherein the sample passage is formed having opposite sample passage lips defining a sample passage inlet between the blocking chute and the sample area, the sample passage lips being oriented lengthwise and substantially parallel to the blocking chute.

5. The system of claim 1 wherein an attractant is positioned within the sample port substantially behind the blocking chute, whereby living organisms within the fluid sample are attracted toward the sample passage.

6. The system of claim 5 wherein the attractant is a light source.

7. The system of claim 6 wherein the light source is configured to emit light having a wavelength of approximately 530 nm (green).

8. The system of claim 1 wherein an attractant is positioned substantially adjacent the sample passage, whereby living organisms within the fluid sample are attracted toward the sample passage.

9. The system of claim 1 wherein:
    the blocking chute is formed having an inwardly-facing surface; and
    an attractant is positioned on the inwardly-facing surface, whereby living organisms within the fluid sample are attracted toward the sample passage.

10. The system of claim 1 wherein a repellant is positioned within the sample area substantially adjacent to the non-sample drain, whereby living organisms are discouraged from entering the non-sample drain.

11. The system of claim 10 wherein the repellant is an acoustic source configured to simulate a predator.

12. The system of claim 1 wherein the sampling probe is an isokinetic probe formed having a proximal end substantially adjacent the flow pipe and an opposite distal end suspended substantially centrally within the flow pipe, the distal end defining a sampling tip orifice.

13. The system of claim 12 wherein a debris screen is positioned within the flow pipe upstream of the distal end of the sampling probe.

14. The system of claim 13 wherein a bubble collapsing screen is positioned within the flow pipe between the debris screen and the distal end of the sampling probe.

15. A system for acquiring a fluid sample, comprising:
    a curved separating pipe terminating in a sample area; and
    a lengthwise inwardly-opening sample passage in fluid communication between at least a portion of the sample area and a sample port, the sample passage defining a sample passage inlet and an interior sample passage surface and being further formed with a substantially lengthwise blocking chute suspended therein, the blocking chute being substantially spaced from the interior sample passage surface so as to form fluid flow pathways about the blocking chute through the sample passage and being formed having a substantially concave inwardly-facing surface, whereby inertial effects induced in the separating pipe cause relatively higher density inorganic and dead organic material to funnel out a non-sample drain formed in the sample area substantially opposite the separating pipe and further whereby inorganic and dead organic material is deflected off the inwardly-facing surface of the blocking chute and otherwise funneled therealong toward the non-sample drain while allowing live organisms to navigate the sample passage around the blocking chute and out the sample port.

16. A system for acquiring a fluid sample, comprising:
a curved separating pipe having formed therein an inwardly-opening lengthwise channel along the outside curve thereof, the channel being recessed relative to the curved separating pipe, the separating pipe terminating in a sample area; and
a lengthwise inwardly-opening sample passage in fluid communication between at least a portion of the sample area and a sample port, the sample passage being formed substantially opposite the channel, whereby inertial effects induced in the separating pipe cause relatively higher density inorganic and dead organic material to funnel toward the channel and out a non-sample drain formed in the sample area substantially opposite the separating pipe while allowing live organisms to navigate the sample passage and out the sample port.

17. The system of claim 16 wherein an attractant is positioned within the sample passage, whereby living organisms within the fluid sample are attracted toward the sample passage.

18. The system of claim 17 wherein the attractant is one or more of a light source and an acoustic source.

19. The system of claim 16 wherein a repellant is positioned within the sample area, whereby living organisms within the fluid sample are repelled toward the sample passage.

20. The system of claim 19 wherein the repellant is one or more of a light source and an acoustic source.

21. The system of claim 16 wherein the channel comprises at least one particle return in fluid communication with a particle return line, whereby at least a portion of the relatively higher density inorganic and dead organic material inertially funneled toward the channel flows through the at least one particle return and the particle return line.

* * * * *